US008981130B2

(12) United States Patent
de Silva et al.

(10) Patent No.: US 8,981,130 B2
(45) Date of Patent: *Mar. 17, 2015

(54) PROCESS FOR THE PRODUCTION OF HEXANEDIOLS

(71) Applicant: E I du Pont de Nemours and Company, Wilmington, DE (US)

(72) Inventors: Wathudura Indika Namal de Silva, Wilmington, DE (US); Ekaterini Korovessi, Wilmington, DE (US); Carl Andrew Menning, Newark, DE (US); Joseph E Murphy, Woodbury, NJ (US); Joachim C Ritter, Wilmington, DE (US); Sourav Kumar Sengupta, Wilmington, DE (US)

(73) Assignee: E I Du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/729,390

(22) Filed: Dec. 28, 2012

(65) Prior Publication Data

US 2013/0172579 A1   Jul. 4, 2013

Related U.S. Application Data

(60) Provisional application No. 61/582,069, filed on Dec. 30, 2011.

(51) Int. Cl.
*C07C 29/60* (2006.01)
*C07D 309/06* (2006.01)

(52) U.S. Cl.
CPC .............. *C07C 29/60* (2013.01); *C07D 309/06* (2013.01); *C07C 2101/14* (2013.01)
USPC .......................................... 549/427; 568/833

(58) Field of Classification Search
CPC ... C07C 29/60; C07C 2101/14; C07D 309/06
USPC .............................. 568/861, 833; 549/427, 402
See application file for complete search history.

(56) References Cited

U.S. PATENT DOCUMENTS

| | | |
|---|---|---|
| 2,082,025 A | 6/1937 | Peters, Jr. |
| 2,201,347 A | 5/1940 | Rittmeister |
| 2,440,929 A | 5/1948 | Frederick |
| 2,768,213 A | 10/1956 | Whetstone et al. |
| 3,070,633 A | 12/1962 | Utne et al. |
| 3,083,236 A | 3/1963 | Utne et al. |
| 3,189,651 A | 6/1965 | Ellery et al. |
| 3,215,742 A | 11/1965 | Horlenko et al. |
| 3,223,714 A | 12/1965 | Manly et al. |
| 3,268,588 A | 8/1966 | Horlenko et al. |
| 3,270,059 A | 8/1966 | Winderl et al. |
| 3,917,707 A | 11/1975 | Williams et al. |
| 3,933,930 A | 1/1976 | Dougherty et al. |
| 4,254,059 A | 3/1981 | Grey |
| 4,400,468 A | 8/1983 | Faber |
| 4,401,823 A * | 8/1983 | Arena ........................... 549/356 |
| 4,780,552 A | 10/1988 | Wambach et al. |
| 5,112,994 A | 5/1992 | Koseki et al. |
| 5,210,335 A | 5/1993 | Schuster et al. |
| 5,412,111 A | 5/1995 | Matsumoto et al. |
| 5,538,891 A | 7/1996 | Schneider et al. |
| 5,696,303 A | 12/1997 | Darsow et al. |
| 5,981,769 A | 11/1999 | Baur et al. |
| 6,008,418 A | 12/1999 | Baur et al. |
| 6,087,296 A | 7/2000 | Harper et al. |
| 6,147,208 A | 11/2000 | Achhammer et al. |
| 6,265,602 B1 | 7/2001 | Voit et al. |
| 6,403,845 B1 | 6/2002 | Pfeffinger et al. |
| 6,407,294 B1 | 6/2002 | Breitscheidel et al. |
| 6,433,192 B1 | 8/2002 | Fischer et al. |
| 6,462,220 B1 | 10/2002 | Luyken et al. |
| 6,593,481 B1 | 7/2003 | Manzer |
| 6,818,781 B2 | 11/2004 | Bhatia |
| 7,019,155 B2 | 3/2006 | Manzer |
| 7,230,145 B2 | 6/2007 | Kadowaki et al. |
| 8,053,608 B2 | 11/2011 | Kouno et al. |
| 8,053,615 B2 | 11/2011 | Cortright et al. |
| 8,501,989 B2 | 8/2013 | Boussie et al. |
| 8,524,925 B2 | 9/2013 | Sabesan et al. |
| 8,669,393 B2 | 3/2014 | Boussie et al. |
| 2003/0212298 A1 | 11/2003 | Brasse et al. |
| 2006/0014988 A1 | 1/2006 | Fischer et al. |
| 2007/0287845 A1 | 12/2007 | Lilga et al. |
| 2008/0200698 A1 | 8/2008 | Reichert et al. |
| 2009/0156841 A1 | 6/2009 | Sanborn et al. |
| 2009/0314992 A1 | 12/2009 | Pinkos et al. |

(Continued)

FOREIGN PATENT DOCUMENTS

| | | |
|---|---|---|
| CA | 2800797 A1 | 12/2011 |
| CN | 101628875 A | 1/2010 |

(Continued)

OTHER PUBLICATIONS

Buntara. "Caprolactam from Renewable Resources: Catalytic Conversion of 5-Hydroxymethylfurfural into Caprolactone." Angewandte Chemie International Edition 50.31 (2011): 7083-7087.*
Ott, L. et al., Catalytic dehydration of glycerol in sub- and supercritical water: a new chemical process for acrolein production, Green Chemistry, 2006, pp. 214-220, vol. 8.
Ponder, Glenn R. et al., Pyrolytic Conversion of Biomass of Anhydrosugars—Influences of Indigenous Ions and Polysaccharide Structures, Applied Biochemistry and Biotechnology, 1990, pp. 41-47, vol. 24/25.
Shafizadeh, Fred et al., Some Reactions of Levoglucosenone, Carbohydrate Research, 1979, pp. 169-191, vol. 71.
International Search Report dated Apr. 29, 2013, International Application No. PCT/US2012/071891.

(Continued)

*Primary Examiner* — Noble Jarrell
*Assistant Examiner* — John Mauro

(57) ABSTRACT

Disclosed are processes for preparing 1,2-cyclohexanediol, and mixtures of 1,2-cyclohexanediol and 1,6-hexanediol, by hydrogenating 1,2,6-hexanetriol.

14 Claims, No Drawings

(56) References Cited

U.S. PATENT DOCUMENTS

| | | | |
|---|---|---|---|
| 2010/0113841 A1* | 5/2010 | Suzuki et al. | 568/852 |
| 2010/0216958 A1 | 8/2010 | Peters et al. | |
| 2010/0274030 A1 | 10/2010 | Bevinakatti et al. | |
| 2010/0317822 A1 | 12/2010 | Boussie et al. | |
| 2011/0040131 A1* | 2/2011 | Kouno et al. | 568/861 |
| 2011/0071306 A1 | 3/2011 | Robinson | |
| 2011/0218318 A1 | 9/2011 | Boussie et al. | |
| 2011/0263916 A1 | 10/2011 | Bao et al. | |
| 2011/0312051 A1 | 12/2011 | Kalnes et al. | |
| 2012/0010419 A1 | 1/2012 | Pinkos et al. | |
| 2012/0022298 A1 | 1/2012 | Pinkos et al. | |
| 2012/0035399 A1 | 2/2012 | Abillard et al. | |
| 2012/0059174 A1 | 3/2012 | Abillard et al. | |
| 2012/0116122 A1 | 5/2012 | Feist et al. | |
| 2012/0172579 A1 | 7/2012 | Qiao et al. | |
| 2013/0172578 A1 | 7/2013 | Allgeier et al. | |
| 2013/0172580 A1 | 7/2013 | Ritter et al. | |
| 2013/0172586 A1 | 7/2013 | DeSilva et al. | |
| 2013/0172629 A1 | 7/2013 | Allgeier et al. | |
| 2013/0184495 A1 | 7/2013 | Dias et al. | |
| 2013/0231505 A1 | 9/2013 | Allgeier et al. | |
| 2013/0289311 A1 | 10/2013 | Allgeier et al. | |
| 2013/0289312 A1 | 10/2013 | Allgeier et al. | |
| 2013/0289318 A1 | 10/2013 | Allgeier et al. | |
| 2013/0289319 A1 | 10/2013 | Allgeier et al. | |
| 2014/0228596 A1 | 8/2014 | Allgeier et al. | |

FOREIGN PATENT DOCUMENTS

| | | |
|---|---|---|
| CN | 102190639 A | 9/2011 |
| DE | 4238493 C1 | 4/1994 |
| EP | 110089 B1 | 1/1988 |
| EP | 0411403 A1 | 2/1991 |
| EP | 0418925 A2 | 3/1991 |
| EP | 1243573 A1 | 9/2002 |
| EP | 1243673 A1 | 9/2002 |
| EP | 2390247 A1 | 11/2011 |
| JP | 04041449 A | 2/1992 |
| JP | 04046133 A | 2/1992 |
| JP | 2003183200 A | 7/2003 |
| JP | 2006036653 A | 2/2006 |
| JP | 04555475 B2 | 9/2010 |
| KR | 100645668 B1 | 11/2006 |
| KR | 100688765 B1 | 2/2007 |
| WO | 9955654 A1 | 11/1999 |
| WO | 2007103586 A2 | 9/2007 |
| WO | 2007103586 A3 | 9/2007 |
| WO | 2009126852 A1 | 10/2009 |
| WO | 2009133787 A1 | 11/2009 |
| WO | 2010033789 A2 | 3/2010 |
| WO | 2010033789 A3 | 3/2010 |
| WO | 2010062689 A2 | 6/2010 |
| WO | 2010099201 A1 | 9/2010 |
| WO | 2010115759 A2 | 10/2010 |
| WO | 2010115759 A3 | 10/2010 |
| WO | 2010144873 A1 | 12/2010 |
| WO | 2011149339 A1 | 12/2011 |
| WO | 2013027766 A1 | 2/2013 |
| WO | 2013066776 A1 | 5/2013 |
| WO | 2013109477 A1 | 7/2013 |

OTHER PUBLICATIONS

Buntara, Teddy et al., Caprolactam from Renewable Resources: Catalytic Conversion of 5-Hydroxymethylfurfural into Caprolactone, Angewandte Chemie International Edition, 2011, pp. 1-6, vol. 50.
Co-pending application CL5732USNP published as US-2013-0289311-A1.
Co-pending application CL5516 USNP pubiished as 2013-0172586-A1.
Co-pending application CL5590USNP published as US-2013-0172578-A1.
Co-pending application CL5601 USNP published as US-2013-0172580-A1.
Co-pending application CL5600 USNP published as US-2013-0172829-A1.
Co-pending application CL5275 USNP published as US-2013-0289318-A1.
Co-pending application CL5734 USNP published as US-2013-0289312-A1.
Co-pending application CL6020 USNP published as US-2013-0289319-A1.
Co-pending application CL5600 USCIP published as US-2013-0231505-A1.
Co-pending application CL5590 USCIP, U.S. Appl. No. 13/870,095.
Fogler Elements of Chemical Reaction Engineering, 2nd Edition, Prentice-Hall (1992) [Book].
International Search Report dated Mar. 29, 2013, PCT/US2012/062314 [for CL5514 PCT].
International Search Report dated Apr. 29, 2013, PCT/US2012/071907 [for CL5516 PCT].
International Search Report dated Apr. 29, 2013, PCT/US2012/071893 [for CL5590 PCT].
International Search Report dated Apr. 29, 2013, PCT/US2012/071912 [for CL5600 PCT].
International Search Report dated Apr. 30, 2013, PCT/US2012/071894 [for CL5601 PCT].
International Search Report dated Jul. 26, 2013, PCT/US2013/038403 [for CL5275 PCT].
International Search Report dated Jul. 18, 2013, PCT/US2013/038418 [for CL5732 PCT].
International Search Report dated Jul. 24, 2013, PCT/US2013/038441 [for CL6020 PCT].
International Search Report dated Jul. 24, 2013, PCT/US2013/038436 [for CL5734 PCT].
Office actions dated Jun. 26, 2013 and Sep. 13, 2013 for this U.S. Appl. No. 13/729,390 [CL5513 USNP].
Office actions dated Sep. 27, 2013 and Dec. 17, 2013 for copending U.S. Appl. No. 13/729,464 [CL5590 USNP].
Notice of allowance dated Oct. 1, 2013 for copending U.S. Appl. No. 13/729,494 [CL5600 USNP].
Notice of allowance dated Nov. 19, 2013 for copending U.S. Appl. No. 13/729,401 [CL5516 USNP].
Office action dated Dec. 20, 2013 for copending U.S. Appl. No. 13/729,507 [CL5601 USNP].
Abe, R. et al, "Photocatalytic overall water splitting under visible light by TaON and WO3 with an IO3-/I- shuttle redox mediator", Chem Commun, 2005, 3829-3831.
Adkins, H. et al, "The catalytic hydrogenation of organic compounds over copper chromite", J Am Chem Soc (1931), vol. 53, 1093.
Alexeev, O.S. et al, "gamma-Al2O3-Supported Pt catalysts with extremely high dispersions resulting from Pt-W interactions", J Catal , 190 (2000) 157-17.
Binder et al., "Simple chemical transformation of lignocellulosic biomass into furans for fuels and chemicals", J Am Chem Soc (2009) 131, 1979-1985.
Blanc, B. et al, "Starch-derived polyols for polymer technologies: preparation by hydrogenolysis on metal catalysts", Green Chemistry, Apr. 2000, 89-91.
Buntara, T. et al, "Caprolactam from Renewable Resources: Catalytic Conversion of 5-Hydroxymethylfurfural into Caprolactone", Angew. Chem. Int. Ed. (2011), 50(31), 7083-7087.
Buntara, T. et al., "From 5-hydroxymethylfurfural (HMF) to polymer precursors: catalyst screening studies on the conversion of 1,2,6-hexanetriol to 1,6-hexanediol", Top Catal (2012) 55, 612-619.
Caes et al., "Conversion of Fructose into 5-(Hydroxymethyl)furfural in Sulfolane", ChemSusChem, (2011), 4(3), 353-356.
Chen, K. et al, "Chemoselective hydrogenolysis of tetrahydropyran-2-methanol to 1,6-hexanediol over rhenium-modified carbon-supported rhodium catalysts", ChemCatChem (2010) 2, 547-555.
Chen, K. et al, "C-O bond hydrogenolysis of cyclic ethers with OH groups over rhenium-modified supported iridium catalysts", J Catalysis (2012) vol. 294, 171-183.
Chia, M. et al, "Selective hydrogenolysis of polyols and cyclic ethers over bifunctional surface sites on rhodium-rhenium catalysts", J Am Chem Soc (2011) vol. 133, No. 32, 12675-12680.

(56) References Cited

OTHER PUBLICATIONS

Connor, R. et al, "Hydrogenolysis of Oxygenated Organic Compounds", J Am Chem Soc (1932), vol. 54, 4678-4690.
Corma, A. "Inorganic Solid Acids and Their Use in Acid-Catalyzed Hydrocarbon Reactions", (1995) Chem. Rev., 95, 559-614.
Diebold, U. "The surface science of titanium dioxide", Surface Science Reports 48 (2003) 53-229.
Efremov, A.A. et al, "Conversions of Levoglucosenone in Acid Media", Sibirskii Khimicheskii Zhurnal 92, 6, 34-39 Translation.
Efremov, A.A., "Transformations of levoglucosenone at the anhydroglucoside bond", Chem Natural Compounds (1998) 34, 5, 582-589.
Efremov, A.A. et al, "New thermocatalytic methods of chemicals producing from lignocellulosic materials in the presence of acid-type catalysts", Intl Symposium Wood Pulping Chemistry, 8th, Helsinki (1995) 689-696.
French, G.J. et al, "A re-investigation of the thermal decomposition of ammonium paratungstate", J. Mat. Sci, 16 (1981) 3427-3436.
Gong, L. et al, "Selective hydrogenolysis of glycerol to 1,3-propanediol over a Pt/WO3/TiO2/SiO2 catalyst in aqueous media", Appl Catal A General 390 (2010) 119-126.
Gong, X.Q. et al, "Small Au and Pt Clusters at the Anatase TiO2(101) Surface: Behavior at Terraces, Steps, and Surface Oxygen Vacancies", J. Am. Chem. Soc. 130 (2008) 370-381.
Helberger et al, Justus Liebigs Annalen der Chemie (1949) 561, 215-220.
Huang, L. et al, "Direct conversion of glycerol into 1,3-propanediol over Cu-H4SiW12O40/SiO2 in vapor phase", Catal Lett, 131 (2009) 312-320.
Jae, J. et al, "Investigation into the shape selectivity of zeolite catalysts for biomass conversion", Journal of Catalysis (2011) 279, 257-268.
Jalil, P.A. et al, "A Study of Stability of Tungstophosphoric Acid, H3PW12O40, Using Synchrotron XPS, XANES, Hexane Cracking, XRD and IR Spectroscopy", J. Catalysis, 2003, 217(2), 292-297.
Jayaraman, S. et al, "Synthesis and Characterization of Pt-WO3 as Methanol Oxidation Catalysts for Fuel Cells", J Phys Chem B, 2005, 109, 22958-22966.
Jung, M.E. et al, "Synthesis of Methylene-Expanded 2',3'-Dideoxyribonucleosides", J Organic Chemistry 63 (1998) 8133-8144.
Kamalakar, G. et al, "tert-Butylation of Phenol over Ordered Solid Acid Catalysts in Supercritical Carbon Dioxide: Efficient Synthesis of 2,4-Di-tert-butylphenol and 2,4,6-Tri-tert-butylphenol", Ind Eng Chem Res, 45 (2006) 6118-6126.
Karinen, R. et al, "Biorefining: heterogeneously catalyzed reactions of carbohydrates for the production of furfural and hydroxymethyfurfural", Chem Sus Chem (2011) 4, 1002-1016.
Kaufmann, W.E. et al, "The use of platinum oxide as a catalyst in the reduction of organic compounds. IV. Reduction of furfural and its derivatives", J Am Chem Soc (1923) 45, 3029-3044.
Kiss, A.B. et al, "Thermal polycondensation of ammonium paratungstate, (NH4)10[W12O40(OH)2].4H2O", J. Materials Sci, 13 (1978) 2541-2547.
Koso, S. et al, "Chemoselective hydrogenolysis of tetrahydrofurfuryl alcohol to 1,5-pentanediol", Chem. Commun. (2009) 2035-2037.
Koso, S. et al, "Promoting effect of Mo on the hydrogenolysis of tetrahydrofurfuryl alcohol to 1,5-pentanediol over Rh/SiO2", J Catalysis 267 (2009), 89-92.
Kuba, S. et al, "Structure and properties of tungstated zirconia catalysts for alkane conversion", J Catalysis, 216 (2003) 353-361.
Lee, U. et al, "Structure of pentasodium trihydrogenhexatungstoplatinate(IV) icosahydrate", Acta Cryst. (1983) C39, 817-819.
Li, N.; Huber, G.W., "Aqueous-phase hydrodeoxygenation of sorbitol with Pt/SiO2-Al2O3: identification of reaction intermediates", Journal of Catalysis (2010) 270, 48-59.
Li, N. et al, "Renewable gasoline from aqueous phase hydrodeoxygenation of aqueous sugar solutions prepared by hydrolysis of maple wood", Green Chemistry 2011, 13, 91-101.
Liu, L. et al, "Mesoporous WO3 supported Pt catalyst for hydrogenolysis of glycerol to 1,3-propanediol", Chin. J Catal., 2012, 33, 1257-1261.
Miftakhov, M.S. et al, "Levoglucosenone: the properties, reactions, and use in fine organic synthesis", Russian Chem Reviews (1994) 63(10) 869-882.
Nakagawa, Y. et al, "Heterogeneous catalysis of the glycerol hydrogenolysis", Catal Sci Technol 2011, 1, 179-190.
Nakagawa, Y. et al., "Production of 1,5-pentanediol from biomass via furfural and tetrahydrofurfuryl alcohol", Catalysis Today 195 (2012) 136-143.
Nikolla, E. et al., "'One-Pot' Synthesis of 5-(Hydroxymethyl)furfural from Carbohydrates Using Tin-Beta Zeolite", ACS Catal. (2011), 1, 408-410.
Okuhara, T. et al, "Insoluble heteropoly compounds as highly active catalysts for liquid-phase reactions", J. Mol. Catal. 74 (1992) 247-256.
Pae, Y.I. et al, "Characterization of NiO-TiO2 modified with WO3 and catalytic activity for acid catalysis", Bull. Korean Chem. Soc. 2004, vol. 25(12), 1881-1888.
Roman-Leshkov, Y. et al., "Solvent effects on fructose dehydration to 5-hydroxymethylfurfural in biphasic systems saturated with inorganic salts", Top Catal (2009) 52:297-303.
SRI Process Economics Program, 31, Hexamethylenediamine Nov. 1967.
Ten Dam, J. et al, "Pt/Al2O3 catalyzed 1,3-propanediol formation from glycerol using tungsten additives", ChemCatChem (2013), 5(2), 497-505.
Tong, X. et al, "Biomass into chemicals: conversion of sugars to furan derivatives by catalytic processes", Appl. Catalysis A General, 385 (2010) 1-13.
Tripathy, P.K. et al, "A comparative study on the thermal decomposition of ammonium p-tungstate in batch and fluidized-bed reactors", Ind Eng Chem Res 36 (1997) 3602-3606.
Trost, B. M. "Cyclizations Made Easy by Transition Metal Catalysts", in Homogeneous Transition Metal Catalyzed Reactions; Moser, W. et al; Adv. Chem. 31, 1992, ACS, Washington, DC.
Xu, W. et al, "Direct catalytic conversion of furfural to 1,5-pentanediol by hydrogenolysis of the furan ring under mild conditions over Pt/Co2AlO4 catalyst" Chem Comm, Royal Society of Chemistry (2011) vol. 47, No. 13, 3924-3926.
Yamazoe, S. et al, "XAFS Study of Tungsten L1-, L3- Edges: Structural Analysis of Loaded Tungsten Oxide Species", Envir Sci, Research Frontiers 2008, Spring 8, 138-139.
Yamazoe, S. et al, "XAFS Study of Tungsten L1- and L3-Edges: Structural Analysis of WO3 Species Loaded on TiO2 as a Catalyst for Photo-oxidation of NH3", J. Phys Chem C 2008, 112, 6869-6879.
Yoshinaga, Y. et al, "Shape-selective oxidation catalysed by a Pt-promoted ultramicroporous heteropoly compound", J.Chem. Soc. Faraday Trans 1998, 94(15) 2235-2240.
Zanardi, M.M. et al, "Synthesis of a simple chiral auxiliary derived from levoglucosenone and its application in a Diels-Alder reaction", Tetrahedron letters 50 (2009) 999-1002.
Notice of allowance dated Mar. 11, 2014 for copending U.S. Appl. No. 13/870,091.
Notice of allowance dated Mar. 26, 2014 for copending U.S. Appl. No. 13/870,072.
Efremov, A.A. et al, "Conversions of Levoglucosenone in Acid Media", Sibirskii Khimicheskii Zhurnal, 1992, 6, 34-39 Translation.
Co-pending application CL5516 USNP published as 2013-0172586-A1, filed Dec. 28, 2012.
Co-pending application CL5590 USNP published as US-2013-0172578-A1, filed Dec. 28, 2012.
Co-pending application CL5600 USNP published as US-2013-0172629-A1, filed Dec. 28, 2012.
Co-pending application CL5601 USNP published as US-2013-0172580-A1, filed Dec. 28, 2012.
Co-pending application CL5275 USNP published as US-2013-0289318-A1, filed Apr. 25, 2013.
Co-pending application CL5732 USNP published as US-2013-0289311-A1, filed Apr. 25, 2013.
Co-pending application CL5734 USNP published as US-2013-0289312-A1, filed Apr. 25, 2013.

(56) References Cited

OTHER PUBLICATIONS

Co-pending application CL6020 USNP published as US-2013-0289319-A1, filed Apr. 25, 2013.
Co-pending application CL5590 USCIP, U.S. Appl. No. 13/870,095, filed Apr. 25, 2013.
Co-pending application CL5600 USCIP published as US-2013-0231505-A1, filed Apr. 25, 2013.
Co-pending application CL5783 USNP, U.S. Appl. No. 14/031,356, filed Sep. 19, 2013.
Co-pending application CL5844 USPSP, U.S. Appl. No. 61/782,172, filed Mar. 14, 2013.
Co-pending application CL5845 USPSP, U.S. Appl. No. 61/782,198, filed Mar. 14, 2013.
Notice of allowance dated Jan. 13, 2014 for copending U.S. Appl. No. 13/729,494 [for CL5600 USNP].
Alamillo, R. et al., "Selective Hydrogenation of Biomass-Derived 5-Hydroxymethylfurfural Using Heterogeneous Catalysts", Green Chem., 2012, 14, 1413.
Jung, K.J. et al., "Furfural Decarbonylation Catalyzed by Charcoal Supported Palladium: Part I—Kinetics", Biomass 16 (1988) 63-76.
Jung, K.J. et al., "Furfural Decarbonylation Catalyzed by Charcoal Supported Palladium: Part II—A Continuous Process", Biomass 16 (1988) 89-96.
Lichtenthaler, F.W. "Carbohydrates as Organic Raw Materials" 2010 Wiley-VCH Verlag GmbH&Co. KGaA, Weinheim 10.1002/14356007.n05_n07.
Qin, L.-Z. et al., "Aqueous-phase deoxygenation of glycerol to 1,3-propanediol over Pt/WO3/ZrO2 catalysts in a fixed-bed reactor", Green Chem., 2010, 12, 1466-1472.
Rao, R.S. et al., "Furfural Hydrogenation Over Carbon-Supported Copper", Catalysis Letters 60 (1999) 51-57.
Zheng, H.-Y. et al., "Towards Understanding the Reaction Pathway in Vapour Phase Hydrogenation of Furfural to 2-Methylfuran", J Molecular Catalysis A: Chemical 246 (2006) 18-23.
International Search Report dated May 6, 2014, PCT/US2012/062314 [for CL5514 PCT].
Copending application No. PCT/US14/23874 [CL5844 WOPCT] filed Mar. 12, 2014.
Copending application No. PCT/US14/23905 [CL5845 WOPCT] filed Mar. 12, 2014.
Notice of allowance dated Apr. 25, 2014 for copending U.S. Appl. No. 13/729,464 [CL5590 USNP].
Notice of allowance dated Apr. 28, 2014 for copending U.S. Appl. No. 13/729,494 [CL5600 USNP].
Notice of allowance dated Apr. 29, 2014 for copending U.S. Appl. No. 13/729,507 [CL5601 USNP].
Database CAPLUS on STN, AN 1979:151575, Nishino et al, JP 53149905 A, Dec. 27, 1978 (abstract).
Database WPIX on STN, AN 1979-11181B [197906], Nishino et al, JP53149905 A Dec. 27, 1978 (abstract).
Notice of allowance dated Jun. 10, 2014 for copending U.S. Appl. No. 13/870,091 [CL6020 USNP].
Notice of allowance dated Jun. 23, 2014 for copending U.S. Appl. No. 13/870,072 [CL5732 USNP].
Notice of allowance dated Jul. 8, 2014 for copending U.S. Appl. No. 13/870,080 [CL5734 USNP].
Notice of allowance dated Jul. 8, 2014 for copending U.S. Appl. No. 13/870,095 [CL5590 USCIP].
Notice of allowance dated Jul. 10, 2014 for copending U.S. Appl. No. 13/729,507 [CL5601 USNP].
Notice of allowance dated Jul. 18, 2014 for copending U.S. Appl. No. 13/870,099 [CL5600 USCIP].
Notice of allowance dated Jul. 22, 2014 for copending U.S. Appl. No. 13/729,401 [CL5516 USNP].
Notice of allowance dated Jul. 22, 2014 for copending U.S. Appl. No. 13/729,464 [CL5590 USNP].
Office action dated Apr. 9, 2014 for copending U.S. Appl. No. 13/870,080 [CL5734 USNP].

\* cited by examiner

PROCESS FOR THE PRODUCTION OF HEXANEDIOLS

This application claims priority under 35 U.S.C. §119(e) from, and claims the benefit of, U.S. Provisional Application No. 61/582,069, filed Dec. 30, 2011, which is by this reference incorporated in its entirety as a part hereof for all purposes.

FIELD OF DISCLOSURE

Processes for preparing 1,2-cyclohexanediol and mixtures of 1,2-cyclohexanediol and 1,6-hexanediol are provided.

BACKGROUND

Industrial chemicals obtained from inexpensive sources are desirable for use in industrial processes, for example as raw materials, solvents, or starting materials. It has become increasingly desirable to obtain industrial chemicals or their precursors from materials that are not only inexpensive but also benign in the environment. Of particular interest are materials which can be obtained from renewable sources, that is, materials that are produced by a biological activity such as planting, farming, or harvesting. As used herein, the terms "renewable" and "biosourced" can be used interchangeably.

1,2-Cyclohexanediol and related compounds such as 1,6-hexanediol are useful precursors in the synthesis of industrially useful chemicals such as pharmaceuticals, herbicides, stabilizers, and polymers. For example, 1,2-cyclohexanediol can be converted to adipic acid, o-phenylenediamine, catechol, phenol, benzoquinone, and hydroquinone. 1,6-Hexanediol is used in the production of polyesters for polyurethane elastomers, coatings, adhesives and polymeric plasticizers. 1,6-Hexanediol can also be converted to 1,6-hexamethylenediamine, a useful monomer in nylon production. Partial oxidation of the petrochemicals cyclohexane and cyclohexene has been used to synthesize 1,2-cyclohexanediol. However, renewable sources for materials such as 1,2-cyclohexanediol and 1,6-hexanediol are desired, in particular renewable sources which are economically attractive in comparison to petroleum-based sources.

There is a need for processes to produce 1,2-cyclohexanediol and other hexanediols from renewable biosources. There is a need for processes to produce 1,2-cyclohexanediol and 1,6-hexanediol from biomass-derived starting materials, including 1,2,6-hexanetriol.

SUMMARY

In one embodiment of the invention disclosed herein, a process is provided comprising: contacting 1,2,6-hexanetriol with hydrogen in the presence of a hydrogenation catalyst at a temperature in the range of from about 120° C. to about 300° C. and at a pressure in the range of from about 200 psi to about 3000 psi to form a product mixture comprising 1,2-cyclohexanediol. In one embodiment, the product mixture further comprises 1,6-hexanediol.

DETAILED DESCRIPTION

As used herein, where the indefinite article "a" or "an" is used with respect to a statement or description of the presence of a step in a process disclosed herein, unless the statement or description explicitly provides to the contrary, the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

As used herein, the term "biomass" refers to any hemicellulosic or lignocellulosic material and includes materials comprising hemicellulose, and optionally further comprising cellulose, lignin, starch, oligosaccharides and/or monosaccharides.

As used herein, the term "lignocellulosic" means comprising both lignin and cellulose. Lignocellulosic material can also comprise hemicellulose. In some embodiments, lignocellulosic material contains glucan and xylan.

Hemicellulose is a non-cellulosic polysaccharide found in lignocellulosic biomass. Hemicellulose is a branched heteropolymer consisting of different sugar monomers. It typically comprises from 500 to 3000 sugar monomeric units.

Lignin is a complex high molecular weight polymer and can comprise guaiacyl units as in softwood lignin, or a mixture of guaiacyl and syringyl units as in hardwood lignin.

As used herein, the abbreviation "126HT" refers to 1,2,6-hexanetriol and includes a racemic mixture of isomers. The chemical structure of 1,2,6-hexanetriol is represented by Formula (I).

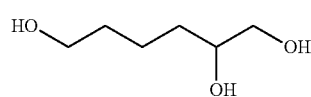

As used herein, the abbreviation "THPM" refers to tetrahydro-2H-pyran-2-methanol, also known as 2-hydroxymethyltetrahydropyran, and includes a racemic mixture of isomers. The chemical structure of tetrahydro-2H-pyran-2-methanol is represented by Formula (II).

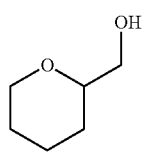

II

As used herein, the abbreviation "16HD" refers to 1,6-hexanediol. The chemical structure of 1,6-hexanediol is represented by Formula (III).

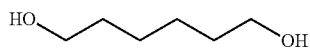

III

As used herein, the abbreviation "12CHD" refers to 1,2-cyclohexanediol and includes a mixture of stereoisomers (cis and racemic trans isomers). As used herein, the abbreviation "c12CHD" refers to cis-1,2-cyclohexanediol. As used herein, the abbreviation "t12CHD" refers to trans-1,2-cyclohexanediol. The chemical structure of 1,2-cyclohexanediol is represented by Formula (IV).

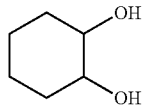

IV

As used herein, the abbreviation "15HD" refers to 1,5-hexanediol and includes a racemic mixture of isomers. The chemical structure of 1,5-hexanediol is represented by Formula (V).

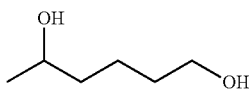

V

As used herein, the abbreviation "15PD" refers to 1,5-pentanediol. The chemical structure of 1,5-pentanediol is represented by Formula (VI).

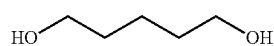

VI

Disclosed herein are processes for obtaining 1,2-cyclohexanediol and mixtures of 1,2-cyclohexanediol and 1,6-hexanediol from 1,2,6-hexanetriol, which in turn can be derived from a renewable biosource. As used herein, the term "renewable biosource" includes biomass and animal or vegetable fats or oils.

A renewable biosource can be pyrolyzed under high temperature conditions in the presence of an acid catalyst to provide useful chemical intermediates. For example, pyrolysis of wood, starch, glucose or cellulose can produce levoglucosenone by known and conventional methods (see, for example, Ponder (*Applied Biochemistry and Biotechnology,* Vol 24/25, 41-47 (1990)) or Shafizadeh (*Carbohydrate Research,* 71, 169-191 (1979)).

Glycerol can be obtained from a renewable biosource, for example from hydrolysis of vegetable and animal fats and oils (that is, triacylglycerides comprising ester functionality resulting from the combination of glycerol with $C_{12}$ or greater fatty acids).

1,2,6-Hexanetriol can be obtained from materials such as glucose, cellulose or glycerol which can be derived from a renewable biosource. For example, 1,2,6-hexanetriol can be obtained by a process comprising the steps of contacting glycerol with a catalyst to prepare acrolein, heating acrolein optionally in the presence of a catalyst to prepare 2-formyl-3,4-dihydro-2H-pyran, contacting 2-formyl-3,4-dihydro-2H-pyran with water to prepare 2-hydroxyadipic aldehyde and contacting 2-hydroxyadipic aldehyde with hydrogen and a catalyst to produce a product mixture comprising 1,2,6-hexanetriol. See, for example, U.S. Pat. No. 2,768,213, German Patent No. 4238493, and L. Ott, et al. in *Green Chem.,* 2006, 8, 214-220.

In the processes disclosed herein, 1,2,6-hexanetriol is contacted with hydrogen in the presence of a hydrogenation catalyst comprising a transition metal under suitable temperature and temperature conditions to form a product mixture comprising 1,2-cyclohexanediol. In some embodiments, the product mixture further comprises 1,6-hexanediol. In some embodiments, the product mixture further comprises one or more of tetrahydro-2H-pyran-2-methanol, 1,5-hexanediol, and 1,5-pentanediol.

The hydrogenation catalyst comprises a transition metal selected from the group consisting of platinum, nickel, cobalt, silver, copper, ruthenium, rhodium, iron, palladium, and mixtures thereof. In some embodiments, the catalyst comprises a transition metal selected from platinum, palladium, copper, nickel, or mixtures thereof. In some embodiments, the catalyst comprises copper.

In some embodiments, the hydrogenation catalyst comprises CuO. In some embodiments, the catalyst comprises from 2 wt % to 98 wt % CuO and further comprises from 98 wt % to 2 wt % of at least one oxide selected from the group consisting of zinc oxide (ZnO), magnesium oxide (MgO), barium oxide (BaO), chromium oxide ($Cr_2O_3$), silica ($SiO_2$), alumina ($Al_2O_3$), zirconium dioxide ($ZrO_2$), nickel oxide (NiO), manganese oxide ($MnO_2$), sodium oxide ($Na_2O$), potassium oxide ($K_2O$), cerium oxide ($CeO_2$), lanthanum oxide ($La_2O_3$), iron oxide ($Fe_2O_3$), silver oxide ($Ag_2O$) and cobalt oxide ($Co_2O_3$), based on the total weight of the catalyst. In one embodiment, the catalyst further comprises ZnO. In one embodiment, the catalyst further comprises MgO. In some embodiments, the catalyst further comprises carbon. Examples of suitable commercially available catalysts include but are not limited to the following: CuO/ZnO, BaO/CuO/$Cr_2O_3$/$SiO_2$, BaO/CuO/$Cr_2O_3$, BaO/CuO/$MnO_2$/$Cr_2O_3$, CuO/$SiO_2$, CuO/$Al_2O_3$, CuO/NiO/$Al_2O_3$, CuO/$Cr_2O_3$/$MnO_2$, CuO/$Cr_2O_3$, CuO/$MnO_2$, CuO/$Cr_2O_3$, CuO/ZnO/$Al_2O_3$, CuO/$SiO_2$/$Cr_2O_3$/MgO, CuO/ZnO/$CeO_2$/$Al_2O_3$/$Na_2O$/C, CuO/NiO, or NiO/CuO/$K_2O$/$Cr_2O_3$/$CaF_2$. In one embodiment, the catalyst comprises CuO/ZnO, CuO/ZnO/$Al_2O_3$, or CuO/ZnO/$CeO_2$/$Al_2O_3$/$Na_2O$/C.

In some embodiments, catalysts comprising CuO can further comprise a support. Examples of suitable supports include aluminas, zeolites, $CeO_2$, $ZrO_2$, MgO, $MgAl_2O_4$, and $TiO_2$. In some embodiments, the supports are impregnated with promoters, such as Ba, La, Mg, Ca, Na, and K. Examples of suitable supported copper catalysts include $CuO/La_2O_3/ZrO_2$, $CuO/La_2O_3/Al_2O_3$, $CuO/CeO_2/ZrO_2$, and $CuO/MgO$. Specific examples of suitable catalysts include $ZrO_2$ 15% La 7% Cu, Sasol Alumina 10% La 3% Cu, Sasol Alumina 10% La 7% Cu, Sasol Alumina 10% La 15% Cu, MEL $Ce/ZrO_2$ 15% Cu, MgO 3% Cu, MgO 7% Cu, and MgO 15% Cu.

Catalysts comprising CuO and at least one oxide as described above can be prepared by forming a co-precipitated catalyst comprising compounds which are thermally decomposable to oxides or mixed oxides.

The precipitated catalyst can be formed by admixing solutions of the elements and heating the resultant mixture to its precipitation temperature; separately heating a solution of a precipitant in water; and thereafter adding both solutions to preheated demineralized water with vigorous stirring and strict pH control, for example in a precipitation reactor. Alternatively, the precipitate can be formed by admixing solutions of the elements and heating the resultant mixture to its precipitation temperature; then adding the preheated mixture or solution of elements rapidly to a predetermined volume of a preheated solution of a precipitant in water. In yet another method of forming a precipitated catalyst, the precipitate can be formed by admixing solutions of the elements and heating the resultant mixture to its precipitation temperature; then adding a preheated solution of precipitant in water (preheated to a predetermined precipitation temperature) to the hot solution or mixture of the elements with vigorous stirring, until the desired pH value of combined solutions is reached. In all methods, the precipitant can be a solution of sodium, potassium and/or ammonium carbonate or bicarbonate in water.

The precipitation can be carried out at high temperature, for example between about 75° C. and 100° C. Lower temperatures, for example between about 50° C. and 60° C. can also be used, but the crystallite size of the catalyst precursor so formed is larger, and the activity of such a catalyst may be lower. The precipitation can be effected at a pH in the range of 6.5-9.5.

After maintaining the stirred solution at the precipitation temperature for a period of time between about 0.5 and 60 minutes, the precipitate can then be separated from the residual liquid. The separation can be effected by filtration. The precipitate can be re-suspended at least once, but typically a few times, in demineralized water, then separated from the water by filtration, and finally washed thoroughly on the filter.

The washed precipitate comprising a homogeneous hydrated catalyst precursor can then be dried by any known drying process, for example in an oven at temperatures between 50° C. and 130° C., under vacuum or at normal pressure. Alternatively, spray drying can be employed.

The dried precipitate, also referred to herein as a precursor, comprises an essentially homogeneous association of carbonates and hydroxycarbonates with a potential oxide content of between 65% and 80%. As described above herein, the elements may initially be in soluble nitrate form or optionally in the form of a thermally decomposable ammonium salt. The dried precipitate can be calcined to provide a catalyst.

The calcination can comprise treating the dried precipitate at a temperature of between 200° C. and 450° C., for example between 250° C. and 350° C., for between 3 and 10 hours, to obtain a homogeneous catalyst.

The homogeneous catalyst can be densified and pelletized after addition of 1-3 wt %, for example about 2 wt %, graphite. It can also be made into extrudates using, for example, methyl cellulose as a binder. The homogeneous catalyst can also be sieved to a desired particle size distribution to be used in batch or continuous stirred tank reactors.

The copper component of the active catalyst contains the copper in a dispersed form, and after activation acts primarily as the active constituent of the catalyst, while the additional oxide component(s) acts primarily but not exclusively as a structural support. An oxide of chromium, zinc, manganese, or barium when present, thus enhances the activity and/or selectivity of the catalyst and its resistance to poisons, while aluminum oxide, zirconium oxide, and silica enhances the stability, abrasion or attrition resistance, mechanical strength, and thermal stability of the active catalyst.

The active catalyst can be reduced by thermal activation to produce an active catalyst in which at least a portion of the copper, and other element(s) present in the catalyst, are in metallic form.

The thermal activation can comprise reduction treatment of the calcined catalyst in a reactor, using a mixture of an inert gas, preferably nitrogen, and at least one reducing gas, such as hydrogen, carbon monoxide or a mixture thereof. The molar ratio between reducing gas and inert gas should be between 1:30 and 1:100. The reduction temperature can be between 100° C. to 280° C., preferably between 130° C. and 240° C., and the pressure can be 0.1 to 1 MPa.

The catalyst is preferably first slowly heated at a rate of 30-50° C./hour under the inert gas at a pressure between 0.6-0.9 MPa, until a temperature between 120° C. and 150° C. has been reached. Thereafter the reduction takes place by adding the reducing gas to the inert gas in a molar ratio as described above, but preferably between 1:50 and 1:40. The temperature is then slowly further increased at a rate of 15-25° C./h to reach a temperature between 190° C. and 210° C. The thermal reductive activation is continued at this temperature for a time period of between 10 and 24 hours. Thereafter, in a final step, the temperature can be increased to between 230° C. and 250° C. and the molar ratio of reducing gas to inert gas adjusted to between 1:10 and 1:6 for a time period of 1-3 hours, in order to complete activation. The reduced catalyst can then be stabilized by passivating the catalyst in a mixture of nitrogen and oxygen to prevent complete oxidation of the catalyst when exposed to air.

In another embodiment, a wide range of commercially available catalyst supports comprising metal oxides, mixed metal oxides or metal-incorporated metal oxides (such as gamma-alumina, La-doped alumina, Ce-doped zirconia, magnesium oxide, and USY zeolite) can be used as supports with the CuO catalyst.

The metals so incorporated in the metal oxide or mixed metal oxide support can be an alkali, an alkaline earth metal, a rare earth metal, or a mixture of one or more such metals. Incorporation of the specified metal or metals onto the metal oxide or mixed metal oxide support can be accomplished by impregnating the support with an aqueous solution of water-soluble salt precursor(s) of metal(s) such as nitrates and acetates by known methods, drying the wetted support, and then calcining the combination of the metal salt(s) and metal oxide or mixed metal oxide support at a temperature of 350° C. up to 600° C. for about 2 to 16 hours to produce a metal-modified metal oxide or mixed metal oxide support(s). The calcining step at 250° C. to 600° C. prior to depositing the copper on the support is necessary. The time of calcining should be sufficient to decompose the metal salt(s) to the metal oxide(s). The total amount of added metal(s) in the support is in the range of 0.5% to 20% by weight based upon the weight of the support.

After incorporation of the metal(s), copper, preferably as copper nitrate, is impregnated on the metal-modified metal oxide or mixed metal oxide support in any manner known to those skilled in the art. The amount of copper deposited will depend on the desired activity of the catalyst, and can be as little as 2% by weight to as much as 20% by weight. The final catalyst composition containing the copper catalyst on the modified support can be in the form of powder, granules, extrudates or tablets, but certain specific characteristics such as surface area and pore volume, for example, are modified by reason of the deposit of copper.

In another embodiment, the catalyst comprising active metal(s) either in the co-precipitated form with other elements, or active metal(s) dispersed on a first oxide, mixed metal oxides or metal-modified metal oxide support, as described herein above can be either physically mixed and sieved to appropriate size, or intimately mixed and optionally co-extruded or pelletized with a second metal oxide, mixed metal oxides or metal-modified metal oxide support. The pelletized or co-extruded catalyst can be optionally crushed and sieved to appropriate size for use in slurry batch, continuous stirred tank, or fixed bed reactors.

The 1,2,6-hexanetriol, catalyst, and hydrogen are contacted at a reaction temperature within the range from about 120° C. and 300° C. and at a pressure within the range from about 200 psi to about 3000 psi for a time sufficient to form a product mixture comprising 1,2-cyclohexanediol as a mixture of cis and trans isomers. In some embodiments, the product mixture can further comprise 1,6-hexanediol. In some embodiments, the 1,2,6-hexanetriol, catalyst, and hydrogen are contacted at a temperature between and optionally including any two of the following values: 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., and 300° C. In some embodiments, the temperature is within the range from about 200° C. to about 290° C., for example between and optionally including any two of the following values: 200° C., 210° C., 220° C., 230° C., 240° C., 250° C., 260° C., 270° C., 280° C., and 290° C. The period of time for contacting is within the range of about 1 minute to about 10 hours.

In one embodiment, the 1,2,6-hexanetriol, catalyst, and hydrogen are contacted at a pressure between 200 and 3000 psi. In some embodiments, the contacting is at a pressure between and optionally including any two of the following values: 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, and 3000 psi. In some embodiments, the contacting is within the range from about 800 to about 1500 psi, for example between and optionally including any two of the following values: 800, 900, 1000, 1100, 1200, 1300, 1400, and 1500 psi.

The reaction can be run in a batch or continuous mode, in liquid phase, gas phase, or biphasic conditions. The process can be carried out is standard reactors as are known in the art. In an embodiment of continuous operation, the reaction can be carried out in a trickle bed reactor, wherein the liquid hourly space velocity is between 0.05 and 10 $h^{-1}$ (mL liquid feed/mL catalyst/h), for example from 0.5 to about 5 $h^{-1}$ (mL liquid feed/mL catalyst/h). In an embodiment of continuous operation, the reaction can be carried out in a trickle bed reactor, wherein the ratio of the gas volumetric flowrate to the liquid volumetric flowrate as measured at ambient conditions (gas to oil ratio) is between 100 and 5,000, for example from 1,000 to about 4,000.

In a batch mode of operation, the amount of catalyst used will depend on the specific equipment configuration and reaction conditions. In some embodiments, the ratio of catalyst weight to 1,2,6-hexanetriol weight ranges from about 0.05 to 2. In some embodiments, this ratio is between and optionally includes any two of the following values: 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, and 2.0.

The 1,2,6-hexanetriol feed in some embodiments is from about 2 wt % to about 50 wt % in water or another suitable solvent. It is anticipated that the reaction could be run at higher concentrations of 1,2,6-hexanetriol in solvent or even with neat 1,2,6-hexanetriol. Suitable solvents include water, a $C_1$-$C_{20}$ alcohol, a $C_2$-$C_{20}$ ether, a $C_2$-$C_{20}$ ester, or mixtures thereof. Examples of suitable alcohols which are commercially available include methanol, ethanol, propanol, butanol, and hexanol. Examples of suitable ethers which are commercially available include dibutylether, dihexylether, methyl-t-butyl-ether, tetrahydrofuran, and dioxane. Examples of suitable esters which are commercially available include ethyl acetate, butyl acetate, methyl butyrate, ethyl butyrate, butyl butyrate and hexyl acetate.

At the end of the designated contacting time, the catalyst can be separated from the product mixture by methods known in the art, for example by filtration. After separation from the catalyst, the product mixture components, including 1,2 cyclohexanediol, 1,6-hexanediol and any unreacted 1,2,6-hexanetriol, can be separated from one another using any appropriate method known in the art, for example, distillation.

In some embodiments, the product mixture comprises 1,2-cyclohexanediol. In some embodiments, the product mixture comprises 1,6-hexanediol. In some embodiments, the product mixture comprises 1,2-cyclohexanediol and 1,6-hexanediol. Depending on the reaction conditions selected, the processes described herein can provide 1,2-cyclohexanediol (as the sum of cis and trans isomers) and 1,6-hexanediol in various relative amounts. In some embodiments, the molar ratio of 1,2-cyclohexanediol to 1,6-hexanediol is in the range of from about 0.1 to about 20. In some embodiments, the molar ratio of trans-1,2-cyclohexanediol to cis-1,2-cyclohexanediol is from 1 to 2.5.

In some embodiments, the product mixture further comprises one or more of 2-hydroxymethyltetrahydropyran, 1,5-hexanediol, and 1,5-pentanediol, which can be useful as chemical intermediates. In one embodiment, the product mixture further comprises tetrahydropyran-2-methanol. In one embodiment, the product mixture further comprises 1,5-hexanediol. In one embodiment, the product mixture further comprises 1,5-pentanediol.

EXAMPLES

The methods described herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

The following abbreviations are used in the examples: "° C." means degrees Celsius; "wt %" means weight percent; "g" means gram(s); "min" means minute(s); "h" means hour(s); "µL" means microliter(s); "wt %" means weight percent; "RV(s)" means reaction vessel(s); "psi" means pounds per square inch; "mg/g" means milligram(s) per gram; "µm" means micrometer(s); "mL" means milliliter(s); "mm" means millimeter(s); "cm" means centimeter(s); "mL/min" means milliliter(s) per minute; "MPa" means megapascal(s); "GC" means gas chromatography; "MS" means "mass spectrometry"; "Conv" means conversion; "LHSV" means liquid hourly space velocity, and "GTO" means gas to oil ratio.

Materials

All commercial materials were used as received unless stated otherwise. 1,2,6-hexanetriol (>=97 GC area % purity) was obtained from Evonik DEGUSSA GmBH, Marl, Germany. Commercial catalysts, catalyst supports and other materials used for catalyst preparation are described in the list below.

Table of Commercially Available Materials Used and Their Sources

| Description | Vendor | Catalog Number | Composition (wt %) |
|---|---|---|---|
| BaO/CuO/ Cr$_2$O$_3$/SiO$_2$ | SuedChemie | G-22/2 | CuO 47%, Cr$_2$O$_3$ 34%, BaO 6%, SiO$_2$ 13% |
| BaO/CuO/ Cr$_2$O$_3$ | SuedChemie | G-22 | CuO 41%, Cr$_2$O3 43%, BaO 12% |
| BaO/CuO/ MnO$_2$/Cr$_2$O$_3$ | SuedChemie | G-99B-0 | CuO 47%, Cr2O3 46%, MnO$_2$ 4%, BaO 2% |
| CuO/Cr$_2$O$_3$ | SuedChemie | T-4466 | CuO 53%, Cr$_2$O$_3$ 45% |
| CuO/MnO$_2$ | SuedChemie | T-4489 | CuO 56%, MnO$_2$ 10%, Al$_2$O$_3$ 34% |
| CuO/ZnO/ Al$_2$O$_3$ | SuedChemie | ActiSorb ® 301 | CuO 53%, ZnO 27%, Al$_2$O$_3$ 20% |
| CuO/ZnO | SuedChemie | T-2130 | CuO 33%, ZnO 66% |
| CuO/Cr$_2$O$_3$/ MnO$_2$ | BASF | Cu-1950P | Copper Chromite 73%, Copper Oxide 21%, Manganese Oxide 5%, Chromium (6+) <0.3% |
| CuO/SiO$_2$ (BASF Cu-0860) | BASF | Cu-0860 | Decan-1-ol 30.0-50.0%, Copper 25.0-40.0%, Silicon dioxide 10.0-20.0%, Calcium oxide 0.0-10.0%, Copper oxide 0.0-10.0%, Palygorskite 7 0.0-7.0%, Crystalline silica 0.0-1.0% |
| CuO/SiO$_2$ (Evonik CPCAT 9/1593) | Evonik | CPCAT 9/1593 | CuO 0-40%, Cu$_2$O 0-40%, Na$_2$O$_3$Si 0-5%, SiO$_2$ >40% |
| CuO/NiO/ Al$_2$O$_3$ | Evonik | CPCAT 9/1596 | Al$_2$O$_3$ 45-90%, Cr$_2$O$_3$ 0-5%, CuO 0-25%, NiO 0-25% |
| CuO/Al$_2$O$_3$ | Evonik | CPCAT 9/1597 | Al$_2$O$_3$ 45-90%, Cr$_2$O$_3$ 0-5%, CuO 0-25% |
| CuO/ZnO/ CeO$_2$/ Al$_2$O$_3$/ Na$_2$O/C | Johnson Matthey | PRICAT CZ 30/18 T 6*5 mm | CuO 39%, ZnO 45%, Ce$_2$O$_3$ 2%, Al$_2$O3 8%, Na$_2$O 0.3%, Graphite 2.5%, H$_2$O, CO$_2$ Balance |
| CuO/SiO$_2$/ Cr$_2$O$_3$/MgO | Johnson Matthey | PRICAT CU 60/35 P | CuO 78%, SiO$_2$ 14.5%, Cr$_2$O$_3$ 1.5%, MgO 3%, H$_2$O, CO$_2$ Balance |
| CuO/NiO | Shepherd Chemical | LB 3307 | Copper 27.5%, Nickel 26.5%, Balance Carbonate |
| HY CBV780 | Zeolyst | CBV780 | SiO$_2$/Al$_2$O$_3$ mole ratio:80 |
| ZrO$_2$ | Saint-Gobain-NorPro | SZ31107 | |
| Nb$_2$O$_5$ | Aldrich | #208515 | |
| Sasol Alumina 3% La | Sasol | PURALOX SCFa-140/L3 | Sasol Alumina doped with 3% Lanthanum |
| Sasol Alumina 10% La | Sasol | PURALOX SCFa-140/L10 | Sasol Alumina doped with 10% Lanthanum |
| MEL Ce/ZrO$_2$ | MEL Chemicals | XZO 1291— Ce/ZrO$_2$ | CeO$_2$ 15%, La$_2$O$_3$ 4.4% |
| MgO | Sigma-Aldrich Chemie GmbH | 34.279-3 | |
| ZrO$_2$WO$_3$ | MEL Chemicals | XZO 1250 | 15% WO$_3$ (on ZrO$_2$ basis) |
| La(NO$_3$)3 x XH$_2$O | Sigma-Aldrich Chemie GmbH | 018545-238554 | X = 3 – 5 |
| Ba(NO$_3$)$_2$ | Sigma-Aldrich Chemie GmbH | 217581 | 99.1% purity |
| Cu(NO$_3$)$_2$ x 2.5H$_2$O | Sigma-Aldrich Chemie GmbH | 12837 | 98.2% purity |

The commercial catalysts obtained as shaped materials (tablets, extrudates, spheres, etc.) were crushed and sieved to 0.125-0.160 mm prior to loading into the continuous reactor. The commercial catalysts obtained in powder form were press-pelleted, crushed, and sieved to 0.125-0.160 mm prior to loading in the continuous reactor.

Catalyst Preparation Method I

Catalyst samples referred to as "Catalyst A intimately mixed with Catalyst B" were prepared using the following procedure. If either catalyst A or catalyst B was originally a shaped material (tablets, extrudates, spheres, etc.), it was first crushed to powder form (<125 µm). Four mL of each catalyst were combined and mixed together in a 25 mL glass vial by shaking for a minimum of 30 seconds. The mixture was then screened using a 250 µm sieve. The sieved material was press-pelleted, crushed, and sieved to 0.125-0.160 mm prior to loading into the continuous reactor.

Catalyst Preparation Method II

Catalyst samples referred to as "Catalyst A separately mixed with Catalyst B" were prepared using the following procedure. If either catalyst A or catalyst B was originally a shaped material (tablets, extrudates, spheres, etc.), it was first crushed and sieved to 0.125-0.160 mm. If either catalyst A or catalyst B was originally in powder form, it was first press-pelleted, crushed, and sieved to 0.125-0.160 mm. Four mL of each catalyst were combined and mixed together in a 25 mL glass vial by shaking for minimum of 30 seconds.

Catalyst Preparation Method III

Catalyst samples referred to as "supported copper catalysts" were prepared using the following procedure. Supports used in this catalyst preparation method include: Sasol Alumina 3% La, Sasol Alumina 10% La, MEL Ce/ZrO$_2$ MgO, and HY CBV780. If the support was originally a shaped material (tablets, extrudates, spheres, etc.), it was crushed and sieved to 0.125-0.160 mm. If the support was originally in powder form it was press-pelleted, crushed, and sieved to 0.125-0.160 mm. The support was optionally impregnated with La or Ba at ambient conditions, in a porcelain dish mixed in a lab-shaker with the appropriate concentration of La(NO$_3$)$_3$×XH$_2$O or Ba(NO$_3$)$_2$ solution using incipient wetness technique. The mixture was dried at 80° C. in a vented oven. The dried catalyst was calcined in a muffle furnace at 300° C. for 4 h, ramp rate 1° C./min, in air.

The support, or the La/Ba impregnated support, was subsequently impregnated with Cu at ambient conditions, in a porcelain dish mixed in a lab-shaker with the appropriate concentration of Cu(NO$_3$)$_2$×2.5H$_2$O solution using incipient wetness technique. The mixture was dried at 80° C. in a vented oven. The dried catalyst was calcined in a muffle furnace at 300° C. for 4 h at a ramp rate of 1° C./min in air. The calcined Cu impregnated catalyst was sieved to 0.125-0.160 mm. The catalyst was reduced using 5% H$_2$ in N$_2$ at temperatures determined by differential scanning calorimetry (DSC) analysis (1-2 dwells at 180-330° C., dwell time=2 h, cooling to ambient temperature under $N_2$.)

Continuous Reactor Operation Procedure

Unless otherwise specified, the reactions described in Examples 2-6 were carried out in a stainless steel (SS316) continuous trickle bed reactor (ID=0.4 cm) using the following procedure.

The reactor was packed with approximately 1 mL of catalyst. If the catalyst was not pre-reduced, the following procedure was used for in situ reduction: the reactor was heated at a rate of 1° C./min under forming gas (5% $H_2$ in $N_2$) to the desired reduction temperature (see examples), where it was held for the desired hold-up time, typically 2-3 hours. The pre-reduced or in-situ reduced catalyst was used for running multiple reactions under varying reaction conditions (temperature, pressure, feed concentrations). The reactor temperature was adjusted to the target first reaction condition temperature and held overnight under forming gas and either water or aqueous substrate solution. Subsequently the first reaction condition started by changing the gas feed to 100% $H_2$ and the liquid feed to the desired aqueous substrate concentration. The liquid volumetric feed rate was adjusted to correspond to a target liquid hourly space velocity (LHSV), which was measured in units of mL liquid feed/mL catalyst/h. Unless otherwise specified, the ratio of the gas volumetric flowrate to the liquid volumetric flowrate as measured at ambient conditions (gas to oil ratio, GTO) was adjusted to a value of 4,000. Liquid effluent samples at each reaction condition were taken after continuous operation for a minimum of 24 hours. The liquid samples were analyzed by quantitative GC analysis.

Analytical Methods

Reactor feeds and reaction products were analyzed by gas chromatography using standard GC and GC/MS equipment: Agilent 5975C, HP5890, Stabilwax Column Restek Company Bellefonte, Pa. (30 m×0.25 mm, 0.5 micron film thickness). Chemical components of reaction product mixtures were identified by matching their retention times and mass spectra to those of authentic samples.

Example 1

In a stainless steel (SS316) pressure reactor 1 g of 1,2,6-hexanetriol was dissolved in 9 mL of water and combined with 1 g of catalyst (CuO/ZnO/$Al_2O_3$, Actisorb® 301). The reactor was connected to a high pressure gas manifold and the content was purged with nitrogen gas (1800 psi) 3 times before hydrogen was added. The approximate target amount of hydrogen was added and the reactor was heated to 250° C. and final adjustments to the pressure were made by adding more nitrogen (for 1000 psi target pressure) or hydrogen (for 1800 psi target pressure) to reach the target pressure. After the intended reaction time, the reactor was allowed to cool to room temperature within 2 h and the reaction solutions were filtered through a standard 5 μm disposable filter, diluted with n-propanol and analyzed by GC and GC/MS. Products were identified by matching retention times and mass spectra using known samples. Results for the reactor effluent are given in Table 1. The product distribution at different partial pressures of $H_2$ and the 1,2,6-hexanetriol conversions are given in Table 2.

TABLE 1

Hydrogen Pressure and composition of main components in the volatile reactor effluent (GC area %)

| $P_{H2}$ (psi) at 25° C. | Target P (psi) at 250° C. | THPM | 12CHD | 15HD | 15PD | 16HD | 126HT |
|---|---|---|---|---|---|---|---|
| 200 | 1000 | 23 | 1 | 1 | 1 | 4 | 61 |
| 400 | 1000 | 17 | 7 | 1 | 2 | 3 | 66 |
| 1200 | 1800 | 17 | 8 | 1 | 2 | 5 | 54 |

TABLE 2

Product distribution of main components in the volatile reactor effluent (GC area %)

| $P_{H2}$ (psi) at 25° C. | Target P (psi) at 250° C. | THPM | 12CHD | 15HD | 15PD | 16HD | CONV 126HT |
|---|---|---|---|---|---|---|---|
| 200 | 1000 | 60% | 3% | 3% | 4% | 11% | 39% |
| 400 | 1000 | 53% | 21% | 3% | 5% | 9% | 33% |
| 1200 | 1800 | 38% | 18% | 3% | 5% | 12% | 45% |

Example 2

The continuous reactor was charged with CuO/ZnO (Sued-Chemie T-2130) catalyst. The catalyst was reduced in situ at 250° C. for 3 h. Aqueous solutions of 1,2,6-hexanetriol (2.5 wt %, 10 wt % and 50 wt %) were used as the liquid feed. The liquid volumetric feed rate corresponded to a liquid hourly space velocity (LHSV) equal to 0.5 mL liquid feed/mL catalyst/h. Product yields are given in Table 3 for 240-280° C. under 100 bar $H_2$ pressure.

TABLE 3

Results for Example 2

| Feed Conc. wt % 126HT | Temp. (° C.) | Product Molar Yields (mole %) | | | | | | t12CHD/c12CHD mole ratio | 12CHD/16HD mole ratio | Conv. (%) | Mole Balance (%) |
|---|---|---|---|---|---|---|---|---|---|---|---|
| | | c12CHD | t12CHD | 16HD | THPM | 15HD | 15PD | | | | |
| 2.5 | 240 | 3.40 | 7.67 | 7.51 | 3.32 | 2.00 | 1.79 | 2.25 | 1.48 | 93.47 | 32.91 |
| 2.5 | 260 | 12.79 | 28.80 | 21.31 | 6.69 | 6.58 | 6.55 | 2.25 | 1.95 | 99.71 | 83.32 |
| 2.5 | 280 | 8.62 | 19.98 | 16.46 | 3.75 | 5.35 | 5.07 | 2.32 | 1.74 | 99.99 | 61.31 |
| 10 | 260 | 4.51 | 10.46 | 7.03 | 13.18 | 2.17 | 2.34 | 2.32 | 2.13 | 55.65 | 84.88 |
| 10 | 280 | 10.49 | 23.12 | 14.65 | 9.04 | 5.28 | 4.89 | 2.21 | 2.29 | 88.70 | 80.68 |

TABLE 3-continued

Results for Example 2

| Feed Conc. wt % 126HT | Temp. (°C.) | Product Molar Yields (mole %) | | | | | | t12CHD/c12CHD mole ratio | 12CHD/16HD mole ratio | Conv. (%) | Mole Balance (%) |
|---|---|---|---|---|---|---|---|---|---|---|---|
| | | c12CHD | t12CHD | 16HD | THPM | 15HD | 15PD | | | | |
| 50 | 280 | 5.24 | 10.16 | 3.30 | 14.82 | 1.43 | 2.04 | 1.94 | 4.67 | 39.58 | 97.71 |
| 50 | 260 | 1.16 | 2.27 | 0.75 | 3.39 | 0.31 | 0.57 | 1.95 | 4.59 | 20.38 | 88.28 |
| 50 | 240 | 0.33 | 0.66 | 0.19 | 0.87 | 0.08 | 0.24 | 2.04 | 5.08 | 3.91 | 98.55 |

Example 3

The continuous reactor was charged with $CuO/ZnO/Al_2O_3$ (SuedChemie ActiSorb®301) catalyst. The catalyst was reduced in situ at 250° C. for 3 h. Aqueous solutions of 1,2,6-hexanetriol (2.5 wt %, 10 wt % and 50 wt %) were used as the liquid feed. The liquid volumetric feed rate corresponded to a liquid hourly space velocity (LHSV) equal to 0.5 mL liquid feed/mL catalyst/h. Product yields are given in Table 4 for 240-280° C. under 100 bar $H_2$ pressure.

TABLE 4

Results for Example 3

| Feed Conc. wt % 126HT | Temp. (°C.) | Product Molar Yields (mole %) | | | | | | t12CHD/c12CHD mole ratio | 12CHD/16HD mole ratio | Conv. (%) | Mole Balance (%) |
|---|---|---|---|---|---|---|---|---|---|---|---|
| | | c12CHD | t12CHD | 16HD | THPM | 15HD | 15PD | | | | |
| 2.5 | 240 | 0.99 | 1.83 | 2.96 | 6.63 | 0.58 | 0.70 | 1.85 | 0.95 | 87.43 | 26.78 |
| 2.5 | 260 | 3.46 | 6.53 | 14.29 | 30.53 | 2.26 | 1.49 | 1.89 | 0.70 | 71.86 | 87.20 |
| 2.5 | 280 | 4.52 | 9.18 | 19.96 | 35.47 | 3.65 | 1.83 | 2.03 | 0.69 | 94.26 | 81.04 |
| 10 | 260 | 1.13 | 1.59 | 2.76 | 18.94 | 0.76 | 0.81 | 1.40 | 0.99 | 40.68 | 85.74 |
| 10 | 280 | 2.07 | 3.16 | 8.02 | 49.76 | 1.90 | 1.67 | 1.53 | 0.65 | 82.11 | 85.36 |
| 50 | 280 | 1.78 | 2.37 | 1.60 | 22.55 | 0.68 | 0.72 | 1.33 | 2.59 | 40.93 | 88.89 |
| 50 | 260 | 0.95 | 1.22 | 0.43 | 4.65 | 0.21 | 0.29 | 1.28 | 5.01 | 4.52 | 103.34 |

Example 4

Several continuous reactor runs were performed with the following commercial copper catalysts: ($BaO/CuO/Cr_2O_3/SiO_2$ (SuedChemie G-22/2), $BaO/CuO/Cr_2O_3$ (SuedChemie G-22), $BaO/CuO/MnO_2/Cr_2O_3$ (SuedChemie G-99B-0), $CuO/Cr_2O_3$ (SuedChemie T-4466), $CuO/MnO_2$ (SuedChemie T-4489), $CuO/Cr_2O_3/MnO_2$ (BASF Cu-1950P), $CuO/SiO_2$ (BASF Cu-0860), $CuO/SiO_2$ (EVONIK CPCAT 9/1593), $CuO/NiO/Al_2O_3$ (EVONIK CPCAT 9/1596), $CuO/Al_2O_3$ (EVONIK CPCAT 9/1597), $CuO/ZnO/CeO_2/Al_2O_3/Na_2O/C$ (Johnson Matthey PRICAT CZ 30/18 T 6*5 mm), $CuO/SiO_2/Cr_2O_3/MgO$ (Johnson Matthey PRICAT CU 60/35 P) and $CuO/NiO$ (Shepherd Chemical LB 3307).

The catalysts were reduced in situ at 250° C. for 3 h. Aqueous solutions of 1,2,6-hexanetriol (2.5 wt %, 10 wt % and 50 wt %) were used as the liquid feed. The liquid volumetric feed rate corresponded to a liquid hourly space velocity (LHSV) equal to 0.5 mL liquid feed/mL catalyst/h. Product yields are given in Table 5 for 240-280° C. under 100 bar $H_2$ pressure.

TABLE 5

Results for Example 4

| Catalyst | Feed Conc. wt % 126HT | Temp. (°C.) | Product Molar Yields (mole %) | | | | | | t12CHD/c12CHD mole ratio | 12CHD/16HD mole ratio | Conv (%) | Mole Balance (%) |
|---|---|---|---|---|---|---|---|---|---|---|---|---|
| | | | c12CHD | t12CHD | 16HD | THPM | 15HD | 15PD | | | | |
| $BaO/CuO/Cr_2O_3/SiO_2$ | 2.5 | 260 | 3.48 | 5.06 | 28.91 | 55.22 | 2.94 | 1.27 | 1.45 | 0.30 | 88.69 | 108.97 |
| $BaO/CuO/Cr_2O_3$ (*) | 10 | 280 | 3.50 | 4.96 | 11.10 | 38.65 | 2.68 | 2.10 | 1.42 | 0.76 | 81.66 | 82.26 |
| $BaO/CuO/MnO_2/Cr_2O_3$ | 2.5 | 280 | 5.06 | 10.72 | 21.58 | 35.48 | 4.06 | 1.94 | 2.12 | 0.73 | 95.52 | 84.02 |
| $CuO/Cr_2O_3$ | 50 | 280 | 2.82 | 3.86 | 2.09 | 24.95 | 0.77 | 0.71 | 1.37 | 3.19 | 40.58 | 94.76 |
| $CuO/MnO_2$ (**) | 2.5 | 260 | 7.57 | 18.64 | 23.45 | 25.07 | 2.28 | 3.35 | 2.46 | 1.12 | 99.96 | 80.88 |
| $CuO/Cr_2O_3/MnO_2$ | 2.5 | 260 | 3.45 | 5.65 | 15.66 | 64.65 | 2.18 | 1.15 | 1.64 | 0.58 | 99.86 | 93.72 |
| $CuO/SiO_2$ (BASF Cu-0860) (**) | 2.5 | 280 | 7.85 | 16.08 | 15.39 | 19.28 | 2.37 | 2.66 | 2.05 | 1.55 | 99.92 | 65.34 |

TABLE 5-continued

Results for Example 4

| Catalyst | Feed Conc. wt % 126HT | Temp. (° C.) | Product Molar Yields (mole %) | | | | | | t12CHD/ c12CHD mole ratio | 12CHD/ 16HD mole ratio | Conv (%) | Mole Balance (%) |
|---|---|---|---|---|---|---|---|---|---|---|---|---|
| | | | c12CHD | t12CHD | 16HD | THPM | 15HD | 15PD | | | | |
| CuO/SiO$_2$ (EVONIK CPCAT 9/1593) | 2.5 | 280 | 2.07 | 2.96 | 21.81 | 70.47 | 2.52 | 0.98 | 1.43 | 0.23 | 91.18 | 110.71 |
| CuO/NiO/Al$_2$O$_3$ | 10 | 280 | 1.78 | 2.25 | 3.14 | 52.15 | 0.79 | 17.98 | 1.27 | 1.28 | 98.73 | 86.68 |
| CuO/Al$_2$O$_3$ | 2.5 | 280 | 8.31 | 14.45 | 24.80 | 32.46 | 8.55 | 4.11 | 1.74 | 0.92 | 98.38 | 95.04 |
| CuO/ZnO/CeO$_2$/Al$_2$O$_3$/ Na$_2$O/C | 2.5 | 260 | 9.42 | 22.00 | 18.88 | 7.91 | 4.96 | 6.05 | 2.33 | 1.66 | 81.50 | 89.07 |
| CuO/SiO$_2$/Cr$_2$O$_3$/MgO | 2.5 | 260 | 1.38 | 2.74 | 26.43 | 56.94 | 1.07 | 0.70 | 1.98 | 0.16 | 99.93 | 89.80 |
| CuO/NiO(**) | 2.5 | 280 | 0.47 | 1.12 | 1.35 | 11.90 | 0.37 | 17.25 | 2.41 | 1.18 | 99.84 | 62.03 |

(*) Reaction was run under 150 bar H$_2$ pressure
(**) Reaction was run at LHSV = 2 h$^{-1}$ and GTO = 1,000

Example 5

Several reactor runs were performed with the following CuO/SiO$_2$ catalysts and mixtures of CuO/SiO$_2$ and heterogeneous acidic catalysts: CuO/SiO$_2$ (BASF Cu-0860), CuO/SiO$_2$ (BASF Cu-0860) intimately mixed with HY CBV780, CuO/SiO$_2$ (BASF Cu-0860) separately mixed with HY CBV780, CuO/SiO$_2$ (BASF Cu-0860) intimately mixed with ZrO$_2$ and CuO/SiO$_2$ (BASF Cu-0860) intimately mixed with ZrO$_2$WO$_3$. The mixed catalysts were prepared using the Catalyst Preparation Method I and Catalyst Preparation Method II. The catalysts were reduced in situ at 300° C. for 2 h. A 2.5 wt % aqueous solution of 1,2,6-hexanetriol was used as the liquid feed for all the runs. The liquid feed volumetric feed rate corresponded to a liquid hourly space velocity (LHSV) equal to 0.5 mL liquid feed/mL catalyst/h. Product yields at different temperatures are given in Table 6 for 240-280° C. under 100 bar H$_2$ pressure.

Example 6

The following supported copper catalysts were prepared using the Catalyst Preparation Method III: ZrO$_2$ 15% La 7% Cu, Sasol Alumina 10% La 3% Cu, Sasol Alumina 10% La 7% Cu, Sasol Alumina 10% La 15% Cu, MEL Ce/ZrO$_2$ 15% Cu, MgO 3% Cu, MgO 7% Cu, MgO 15% Cu, HY CBV780 6% La 7% Cu and HY CBV780 6% Ba 7% Cu. A 2.5 wt % aqueous solution of 1,2,6-hexanetriol was used as the liquid feed for all the runs. The liquid feed volumetric feed rate corresponded to a liquid hourly space velocity (LHSV) equal to 0.5 mL liquid feed/mL catalyst/h. Product yields are given in Table 7 for 260-280° C. under 100 bar H$_2$ pressure.

TABLE 6

Results for Example 5

| Catalyst | Temp. (° C.) | Product Molar Yields (mole %) | | | | | | t12CHD/c12CHD mole ratio | 12CHD/16HD mole ratio | Conv. (%) | Mole Balance (%) |
|---|---|---|---|---|---|---|---|---|---|---|---|
| | | c12CHD | t12CHD | 16HD | THPM | 15HD | 15PD | | | | |
| CuO/SiO$_2$ | 240 | 1.94 | 4.25 | 4.59 | 7.30 | 0.82 | 0.73 | 2.19 | 1.35 | 49.90 | 69.70 |
| CuO/SiO$_2$ | 260 | 12.01 | 24.58 | 8.13 | 42.46 | 2.45 | 1.76 | 2.05 | 4.50 | 100.00 | 92.70 |
| CuO/SiO$_2$ | 280 | 6.42 | 14.05 | 19.03 | 16.36 | 1.27 | 1.46 | 2.19 | 1.08 | 100.00 | 60.10 |
| CuO/SiO$_2$ Intimately Mixed with HY CBV780 | 260 | 12.29 | 16.40 | 19.53 | 42.32 | 3.13 | 2.79 | 1.33 | 1.47 | 100.00 | 97.10 |
| CuO/SiO$_2$ Separately Mixed with HY CBV780 | 260 | 12.29 | 20.37 | 21.48 | 46.76 | 3.54 | 3.05 | 1.66 | 1.52 | 100.00 | 108.30 |
| CuO/SiO$_2$ Intimately Mixed with ZrO$_2$WO$_3$ | 260 | 3.37 | 7.44 | 10.99 | 26.06 | 1.59 | 1.29 | 2.21 | 0.98 | 29.30 | 121.40 |
| CuO/SiO$_2$ Intimately Mixed with ZrO$_2$ | 260 | 9.01 | 18.43 | 27.98 | 29.25 | 2.77 | 2.92 | 2.05 | 0.98 | 100.00 | 91.80 |

TABLE 7

Results for Example 6

| Catalyst | Temp. (° C.) | Product Molar Yields (mole %) | | | | | | t12CHD/c12CHD mole ratio | 12CHD/16HD mole ratio | Conv (%) | Mole Balance (%) |
|---|---|---|---|---|---|---|---|---|---|---|---|
| | | c12CHD | t12CHD | 16HD | THPM | 15HD | 15PD | | | | |
| $ZrO_2$ 15% La 7% Cu | 280 | 11.45 | 22.70 | 8.48 | 5.83 | 1.33 | 1.44 | 1.98 | 4.03 | 99.80 | 68.50 |
| Sasol Alumina 10% La 3% Cu | 280 | 17.27 | 24.36 | 10.86 | 9.35 | 2.62 | 4.91 | 1.41 | 3.83 | 86.20 | 91.18 |
| Sasol Alumina 10% La 7% Cu | 280 | 17.03 | 29.38 | 16.45 | 6.73 | 4.17 | 2.52 | 1.73 | 2.82 | 97.00 | 91.08 |
| Sasol Alumina 10% La 15% Cu | 280 | 16.16 | 25.91 | 14.16 | 9.28 | 3.63 | 2.88 | 1.60 | 2.97 | 93.25 | 88.51 |
| MEL Ce/$ZrO_2$ 15% Cu | 260 | 13.62 | 29.67 | 2.64 | 10.49 | 0.84 | 2.40 | 2.18 | 16.42 | 98.95 | 82.09 |
| MgO 3% Cu | 280 | 6.20 | 10.24 | 20.31 | 14.35 | 1.65 | 2.72 | 1.65 | 0.81 | 80.25 | 98.63 |
| MgO 7% Cu | 280 | 7.84 | 15.78 | 32.57 | 8.71 | 5.11 | 3.61 | 2.01 | 0.73 | 100.00 | 87.87 |
| MgO 15% Cu | 280 | 8.10 | 16.95 | 34.28 | 7.87 | 5.70 | 3.86 | 2.09 | 0.73 | 100.00 | 113.82 |
| HY CBV780 6% La 7% Cu(*) | 260 | 1.03 | 1.28 | 5.67 | 56.28 | 0.00 | 0.00 | 1.24 | 0.41 | 56.00 | 110.30 |
| HY CBV780 6% Ba 7% Cu(*) | 260 | 1.54 | 1.56 | 3.07 | 33.36 | 0.00 | 0.00 | 1.02 | 1.01 | 40.80 | 101.30 |

(*)done at 69 bar $H_2$ pressure

What is claimed is:

1. A process comprising contacting 1,2,6-hexanetriol with hydrogen in the presence of a hydrogenation catalyst at a temperature in the range of from about 120° C. to about 300° C. and at a pressure in the range of from about 200 psi to about 3000 psi to form a product mixture comprising 1,2-cyclohexanediol.

2. The process of claim 1, wherein the hydrogenation catalyst comprises a transition metal selected from the group consisting of platinum, nickel, cobalt, rhodium, silver, copper, ruthenium, iron, palladium, and mixtures thereof.

3. The process of claim 1, wherein the catalyst comprises copper.

4. The process of claim 1, wherein the catalyst comprises CuO.

5. The process of claim 1, wherein the catalyst comprises from 2 weight percent to 98 weight percent CuO, and further comprises from 98 weight percent to 2 weight percent of at least one oxide selected from the group consisting of zinc oxide, magnesium oxide, barium oxide, chromium oxide, silica, alumina, zirconium dioxide, nickel oxide, manganese oxide, sodium oxide, potassium oxide, cerium oxide, lanthanum oxide, iron oxide, silver oxide, and cobalt oxide, based on the total weight of the catalyst.

6. The process of claim 5, wherein the catalyst further comprises at least one oxide selected from the group consisting of zirconium dioxide, lanthanum oxide, cerium oxide, zinc oxide, magnesium oxide, silica and alumina.

7. The process of claim 5, wherein the catalyst further comprises zinc oxide.

8. The process of claim 5, wherein the catalyst comprises BaO/CuO/$Cr_2O_3$/$SiO_2$, BaO/CuO/$Cr_2O_3$, BaO/CuO/$MnO_2$/$Cr_2O_3$, CuO/$SiO_2$, CuO/$Al_2O_3$, CuO/NiO/$Al_2O_3$, CuO/$Cr_2O_3$/$MnO_2$, CuO/$Cr_2O_3$, CuO/$MnO_2$, CuO/$Cr_2O_3$, CuO/$SiO_2$/$Cr_2O_3$/MgO, CuO/NiO, NiO/CuO/$K_2O$/$Cr_2O_3$/$CaF_2$, CuO/ZnO, CuO/ZnO/$Al_2O_3$, or CuO/ZnO/$CeO_2$/$Al_2O_3$/$Na_2O$/C.

9. The process of claim 5, wherein the catalyst comprises CuO/$La_2O_3$/$ZrO_2$, CuO/$La_2O_3$/$Al_2O_3$, CuO/$CeO_2$/$ZrO_2$ or CuO/MgO.

10. The process of claim 1, wherein the product mixture further comprises 1,6-hexanediol.

11. The process of claim 1, wherein the product mixture further comprises one or more of 2-hydroxymethyltetrahydropyran, 1,5-hexanediol, and 1,5-pentanediol.

12. The process of claim 1, wherein product mixture further comprises both 1,2-cyclohexanediol and 1,6-hexanediol, and the molar ratio of 1,2-cyclohexanediol to 1,6-hexanediol is in the range of from about 0.1 to 20.

13. The process of claim 8, wherein the temperature is within the range of from about 200° C. to about 290° C., and the pressure is within the range of from about 800 psi to about 1500 psi.

14. The process of claim 9, wherein the temperature is within the range of from about 200° C. to about 290° C., and the pressure is within the range of from about 800 psi to about 1500 psi.

* * * * *